US012485186B2

(12) United States Patent
Rossi et al.

(10) Patent No.: US 12,485,186 B2
(45) Date of Patent: *Dec. 2, 2025

(54) ANTIBODY-MEDIATED CONDITIONING WITH IMMUNOSUPPRESSION TO ENABLE ALLOGENEIC TRANSPLANTATION

(71) Applicants: THE CHILDREN'S MEDICAL CENTER CORPORATION, Boston, MA (US); THE UNITED STATES OF AMERICA, AS REPRESENTED BY THE SECRETARY, DEPARTMENT OF HEALTH AND HUMAN SERVICES, Bethesda, MD (US)

(72) Inventors: Derrick J. Rossi, Newton, MA (US); Agnieszka D. Czechowicz, Irvine, CA (US); Philip M. Murphy, Rockville, MD (US); Zhanzhuo Li, North Potomac, MD (US)

(73) Assignees: The Children's Medical Center Corporation, Boston, MA (US); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 435 days.

This patent is subject to a terminal disclaimer.

(21) Appl. No.: 16/498,572

(22) PCT Filed: Mar. 29, 2018

(86) PCT No.: PCT/US2018/025044

§ 371 (c)(1),
(2) Date: Sep. 27, 2019

(87) PCT Pub. No.: WO2018/183613

PCT Pub. Date: Oct. 4, 2018

(65) Prior Publication Data

US 2020/0188527 A1 Jun. 18, 2020

Related U.S. Application Data

(60) Provisional application No. 62/479,772, filed on Mar. 31, 2017.

(51) Int. Cl.

| | |
|---|---|
| *A61K 47/68* | (2017.01) |
| *A61K 35/12* | (2015.01) |
| *A61K 35/28* | (2015.01) |
| *A61K 39/00* | (2006.01) |
| *A61K 39/395* | (2006.01) |

(Continued)

(52) U.S. Cl.
CPC .......... *A61K 47/6849* (2017.08); *A61K 35/28* (2013.01); *A61K 39/3955* (2013.01); *A61K 45/06* (2013.01); *A61K 47/6825* (2017.08); *A61P 37/06* (2018.01); *A61K 2035/124* (2013.01); *A61K 2039/505* (2013.01)

(58) Field of Classification Search
CPC ............ A61K 47/6849; A61K 47/6825; A61K 35/28; A61K 39/3955; A61K 45/06; A61P 37/06
See application file for complete search history.

(56) References Cited

U.S. PATENT DOCUMENTS 7,892,578 B2 2/2011 Sykes et al.
8,318,905 B2 11/2012 Kroczek
(Continued)

FOREIGN PATENT DOCUMENTS

WO WO1992002551 2/1992
WO WO-9526740 A1 * 10/1995 ............. A61K 35/39
(Continued)

OTHER PUBLICATIONS

The Merck Manuals Online Medical Library, [online]. Merck Research Laboratories, 2006-2007. [retrieved on Oct. 19, 2020]. <URL: https://www.merckmanuals.com/professional/hematology-and-oncology/overview-of-cancer/cellular-and-molecular-basis-of-cancer>. Cellular and Molecular Basis of Cancer (Year: 2020).*
(Continued)

*Primary Examiner* — Daniel E Kolker
*Assistant Examiner* — Peter Johansen
(74) *Attorney, Agent, or Firm* — Greer, Burns & Crain, Ltd.

(57) ABSTRACT

Provided are methods and compositions conditioning a patient for an allogeneic transplantation, wherein the patient's hematopoietic stem cells (HSCs) are depleted with an HSC-depleting composition and the patient is then administered allogeneic cells selected from bone marrow cells, umbilical cord blood cells, hematopoietic stem and progenitor cells (HSPCs), peripheral blood $CD34^+$ cells, and peripheral blood $CD34^+$ and $CD90^+$ cells; optionally the patient is also administered a medicament selected from the group consisting of a T-cell depleting or inhibiting antibody or antibody fragment, NK-cell depleting or inhibiting antibody or antibody fragment, immunosuppressive drug, and any combination thereof. The HSC-depleting composition comprises a compound selected from the group consisting of: an antibody or antibody fragment with specific binding affinity to a protein displayed at the HSC surface, a conjugate comprising an HSC-recognition molecule and a toxin, and any combination thereof.

2 Claims, 6 Drawing Sheets

(51) Int. Cl.
*A61K 45/06* (2006.01)
*A61P 37/06* (2006.01)

(56) References Cited

U.S. PATENT DOCUMENTS

| | | | | |
|---|---|---|---|---|
| 10,111,966 | B2 | 10/2018 | Nixon et al. | |
| 10,392,425 | B2 * | 8/2019 | Poma | A61P 19/02 |
| 10,882,915 | B2 | 1/2021 | Pearse et al. | |
| 10,899,843 | B2 | 1/2021 | Pearse et al. | |
| 2012/0321598 | A1 | 12/2012 | Cicciarelli et al. | |
| 2014/0242037 | A1 | 8/2014 | Dresch et al. | |
| 2016/0324982 | A1 * | 11/2016 | Scadden | A61K 38/164 |
| 2018/0214524 | A1 * | 8/2018 | Weissman | A61P 37/06 |
| 2021/0177949 | A1 | 6/2021 | Weissman et al. | |

FOREIGN PATENT DOCUMENTS

| | | | | |
|---|---|---|---|---|
| WO | WO2004002425 | A1 | 1/2004 | |
| WO | WO-2004002425 | A2 * | 1/2004 | C07K 16/28 |
| WO | WO2008067115 | A2 | 5/2008 | |
| WO | WO2016164745 | A1 | 4/2016 | |
| WO | WO2016164502 | A1 | 10/2016 | |
| WO | WO2016210292 | A1 | 12/2016 | |
| WO | WO2017219029 | A2 | 12/2017 | |

OTHER PUBLICATIONS

Bernardo et al. "The Role of Conditioning in Hematopoietic Stem-Cell Gene Therapy", Hum Gene Ther. Oct. 2016;27(10):741-748. (Year: 2016).*

Saydaminova et al. "Efficient genome editing in hematopoietic stem cells with helper-dependent Ad5/35 vectors expressing site-specific endonucleases under microRNA regulation", Mol Ther Methods Clin Dev. Jan. 14, 2015;1:14057 (Year: 2015).*

Wu et al. "Rapamycin and T cell costimulatory blockade as post-transplant treatment promote fully MHC-mismatched allogeneic bone marrow engraftment under irradiation-free conditioning therapy", Bone Marrow Transplant. Jun. 2002;29(12):949-56 (Year: 2002).*

Czechowicz et al. "Efficient transplantation via antibody-based clearance of hematopoietic stem cell niches", Science. Nov. 23, 2007; 318(5854):1296-9. (Year: 2007).*

Li, et al., "The Macrophage-depleting Agent Clodronate Promotes Durable Hematopoietic Chimerism and Donor-specific Skin Allograft Tolerance in Mice", Scientific Reports, Feb. 26, 2016, pp. 1-10, 6:22143.

Choo et al., "The HLA System: Genetics, Immunology, Clinical Testing, and Clinical Implications", Yonsei Medical Journal, (2007), pp. 11-23, vol. 48, No. 1.

Fernandez-Vina et al., "Identification of a permissible HLA mismatch in hematopoietic stem cell transplantation", Blood, Feb. 20, 2014, pp. 1270-1278, vol. 23, No. 8.

Gyurkocza et al., "Conditioning regimens for hematopoietic cell transplantation: one size does not fit all", BLOOD, Jul. 17, 2014, pp. 322-353, vol. 124, No. 3.

Fricke et al., "Allogeneic Non-Adherent Bone Marrow Cells Facilitate Hematopoietic Recovery But Do Not Lead to Allogeneic Engraftment", Plos One, Jul. 2009, pp.

PCT Notification Concerning Transmittal of International Preliminary Report on Patentability (Chapter I of the Patent Cooperation Treaty) mailed on Oct. 10, 2019 for PCT International Application No. PCT/US2018/025044.

Woolfrey, A. et al., "HLA-C Antigen Mismatch is Associated with Worse Outcome in Unrelated Donor Peripheral Blood Stem Cell Transplantation", American Society for Blood and Marrow Transplant, 2011, pp. 885-892, vol. 17.

Lee, S. et al, "High-resoluation donor-recipient HLA matching contributes to the success of unrelated donor marrow transplantation", Blood, Dec. 15, 2007, pp. 4578-4583, vol. 110, No. 13.

Petersdorf, E. et al., Limits of HLA mismatching in unrelated hematopoietic cell transplantation, Blood, Nov. 2004, pp. 2976-2980, vol. 104, No. 9.

Foeken, LM., "Monitoring the international use of unrelated donors for transplantation: the WMDS annual reports", Bone Marrow Transplantation, 2010, pp. 811-818, vol. 45, No. 5.

* cited by examiner

ANTIBODY-MEDIATED CONDITIONING WITH IMMUNOSUPPRESSION TO ENABLE ALLOGENEIC TRANSPLANTATION

CROSS-REFERENCE TO RELATED APPLICATIONS

This application is the U.S. National phase application corresponding to PCT/US2018/025044 which was assigned an international filing date of Mar. 29, 2018 and associated with publication WO 2018/183613 A1 and which claims priority to U.S. provisional patent application 62/479,772 filed Mar. 31, 2017, the entire disclosures of which are incorporated herein by reference.

STATEMENT OF GOVERNMENT INTEREST

This invention was supported in part by the Intramural Research Program of the National Institute of Allergy and Infectious Diseases (NIAID) and the National Institutes of Health (NIH).

TECHNICAL FIELD

The invention relates to compositions and methods for treating patients who may benefit from selective depletion of their hematopoietic stem cells (HSCs) followed by infusion with allogeneic bone marrow cells, umbilical cord blood cells, and/or hematopoietic stem and progenitor cells (HSPCs) from a donor, including an HLA-mismatched donor.

BACKGROUND

Many patients may benefit from a procedure by which the patient's immune system is conditioned to accept and tolerate a genetic material which the patient's immune system otherwise detects as foreign and rejects. Such patients include, but are not limited to, recipients of an organ or tissue transplant, and patients afflicted by a hematological disorder.

Methods currently known for conditioning a patient to accept a transplant include myeloablation by radiation, chemotherapy and immunosuppressive drugs. Unfortunately, these methods are highly toxic and may trigger many life-threatening side effects, including hematological malignancies, organ damage, organ failure and infections. (Gyurkocza et al. Blood 2014 124:344-353).

In recent years, significant efforts have been made to develop nonmyeloablative conditioning methods, including methods by which the recipient's hematopoietic stem cells are depleted selectively. Such conditioning methods may include the use of monoclonal antibodies as provided in WO 2008/067115 or the use of conjugates which selectively recognize and ablate hematopoietic stem cells, as provided in WO 2016/164502 or WO 2016/164745.

Allogeneic hematopoietic stem cell transplantation (AHSCT) may be used for treating many hematological disorders, but success of AHSCT depends on efficient conditioning of a patient in order to prevent the rejection of donor cells. (Fernandez-Vina et al. Blood 2014 123:1270-1278). The genetic loci implicated in rejection of donor organs are referred to as the major histocompatibility complex (MHC), and the human MHC is also referred to as Human Leukocyte Antigen (HLA). Various MHC alleles are known, including HLA-A, HLA-B, HLA-C, HLA-DRB1, and DQ. Transplants in which patients and their related or unrelated donors (UDs) match in eight MHC alleles (two HLA-A, two HLA-B, two HLA-C, and two HLA-DRB1 loci) have significantly superior outcomes compared with those having even one or two mismatches at these loci. (Fernandez-Vina et al. Blood 2014 123:1270-1278). A patient matched with a donor still has to be conditioned in order to tolerate a graft from the donor. Patients are known to reject organs because of minor mismatched alleles. Even in HLA-matched grafts, many antigenic differences may be present. These antigenic differences, referred to as minor mismatches, are caused by variation in genes outside of the HLA-genes. The minor mismatches can be clinically significant in transplantation. For example, a variation in CD31 has recently emerged as potentially important.

In the United States, 31 to 75% of patients, depending on ethnic background, are able to find an 8/8 HLA-matched unrelated donor. (Foeken et al. Bone Marrow Transplant 2010; 45(5):811-818). For patients who lack 8/8 HLA-matched related or unrelated donors, alternative sources of allogeneic hematopoietic stem cells are HLA-mismatched unrelated donors, cord blood units, or first-degree haploidentical relatives. (Fernandez-Vina et al. Blood 2014 123:1270-1278). Although the use of an unrelated donor with an HLA-mismatch increases access to transplantation, transplants from HLA-mismatched donors are associated with significantly higher risks for mortality and morbidity compared with those from 8/8 HLA matched donors. (Petersdorf et al. Blood 2004; 104(9):2976-2980).

An HLA-mismatch between a recipient and a hematopoietic stem cell donor represents a risk factor for graft rejection/failure and acute graft-versus-host disease (GVHD). (Choo et al. Yonsei Med. J. 2007; 48(1): 11-23). GVHD is believed to be triggered by immunocompetent donor T cells contained in the stem cell products. (Martin et al. Bone Marrow Transplant. 1990; 6:283-289). T-cell depletion of donor marrow results in lower incidence of acute GVHD, but higher incidence of graft failure, graft rejection, malignant disease relapse (i.e., loss of the graft-versus-leukemia effect), impaired immune recovery, and later complication from Epstein-Barr virus-associated lymphoproliferative disorders. (Cornelissen et al. Curr Opin Hematol. 2000; 7:348-352). Methods for depleting T-cells include those in which T-cell depleting antibodies are used, including as described in U.S. Pat. No. 8,318,905, and in Li et al. Sci. Rep. 2016; 6:22143.

The current state of the transplant field provides that the best compatible hematopoietic stem cells are from an identical twin or a genotypically HLA-identical sibling. For those patients who do not have a matched sibling, a related family member who is HLA haploidentical and partially mismatched for the non-shared HLA haplotypes may serve as an acceptable donor, but these transplants have higher risks for acute GVHD, graft failure, and mortality. (Beatty et al. N Engl J Med. 1984; 313:765-771).

A Center for International Blood and Marrow Transplant Research (CIBMTR) study of predominantly bone marrow HSCT performed using myeloablative conditioning suggests that a single HLA-A and -DRB1 mismatch appeared to be more deleterious than a single mismatch at HLA-B or -C. (Lee et al. Blood 2007; 110(13):4576-4583). In contrast, a study evaluating the effect of HLA mismatches in HSCT with peripheral blood stem cells found higher risks for mortality in the transplants presenting one antigen mismatch in HLA-C or one mismatch in HLA-B. (Woolfrey A, Biol Blood Marrow Transplant 2011; 17(6):885-892.)

Efforts have been made to develop methods in which a donor can become a universal donor such that an allogeneic graft from the universal donor is tolerated by any recipient who is not a twin sibling to the donor. These methods render donor cells non-immunoreactive across MHC barriers—for example by deleting beta 2-microglobin gene which leads to little-to-no MHC class 1 expression. However, not all donor cells can be easily genetically manipulated.

Thus, there exists the need for methods by which a patient recipient can be conditioned to tolerate an allogeneic transplant, including from an HLA-mismatched donor, as these methods would improve access to transplants for patients with no HLA-matched donor available. There also exists the need for developing a conditioning method by which a patient recipient can be conditioned into becoming a universal patient recipient who can tolerate an allogeneic transplant from any donor. Conditioning a patient into a universal recipient would also significantly increase a pool of acceptable donors, thus, addressing the need for a universal donor without genetically manipulating the donor's cells.

SUMMARY

Provided are allogeneic transplantation methods in which a patient recipient is conditioned with an HSC-depleting composition. Included is a method of treating a patient which comprises: 1) depleting hematopoietic stem cells (HSCs) of the patient by administering to the patient an HSC-depleting composition; 2) administering to the patient allogeneic cells selected from the group consisting of bone marrow cells, umbilical cord blood cells, hematopoietic stem and progenitor cells (HSPCs), peripheral blood $CD34^+$ cells, peripheral blood $CD34^+$ and $CD90^+$ cells, and any combination thereof from a donor; and 3) optionally administering to the patient a medicament selected from the group consisting of a T-cell depleting or inhibiting antibody or antibody fragment, natural killer (NK) cell depleting or inhibiting antibody or fragment, immunosuppressive drug, and any combination thereof, wherein the medicament is administered during a time period selected from the group consisting of: prior to the administration of the HSC-depleting composition; during administration of the HSC-depleting composition; after the administration of the HSC-depleting composition, but before the administration of the allogeneic cells; during administration of the allogeneic cells; after the administration of the allogeneic cells; and any combination thereof. The HSC-depleting composition comprises a compound selected from the group consisting of: an antibody or antibody fragment with specific binding affinity to a protein displayed at the HSC surface, a conjugate comprising an HSC-recognition molecule and a toxin, and any combination thereof. The donor can be an HLA-mismatched donor.

The method may further comprise transplanting from the same donor to the patient a transplant selected from the group consisting of an organ, tissue, cells, proteins, and any combination thereof.

Various cells can be transplanted to a patient recipient according to this method, including hematopoietic stem cells, induced pluripotent stem cells (iPSCs), cells derived from iPSCs, bone marrow cells, islet cells, neurons, hematopoietic cells, epithelial cells, hepatocytes, cardiomyocytes, keratinocytes, embryonic stem cells (ESCs), cells derived from ESCs, mesenchymal stem cells (MSCs), and cells derived from MSCs.

An organ and/or tissue that can be transplanted according to this method, include kidney, skin, liver, heart, lung, bone marrow, hair follicle, muscle, ligament, nerve, tendon, bone, limb, face, abdominal wall, eye, ear, retina, and any combination thereof.

A suitable HSC-depleting composition for the method may comprise an antibody or antibody fragment selected from the group consisting of: anti-human CD117 antibody or antibody fragment, anti-human CD110 antibody or antibody fragment, anti-human CD201 antibody or antibody fragment, anti-human CD150 antibody or antibody fragment, anti-human CD90 antibody or antibody fragment, anti-human CD27 antibody or antibody fragment, anti-human Esam antibody or antibody fragment, anti-human CD45 antibody or antibody fragment, and any combination thereof. The antibody or antibody fragment may be humanized. The antibody fragment may be selected from the group consisting of Fab, $F(ab)_2$, scFv and diabody. A particularly preferred HSC-depleting composition comprises an anti-human CD117 antibody or antibody fragment.

In some embodiments of the method, a patient is administered i. v. from 0.01 mg/kg to 50 mg/kg of the HSC-depleting composition comprising an antibody or antibody fragment selected from the group consisting of anti-CD117 antibody or antibody fragments, anti-CD110 antibodies or antibody fragments, anti-CD201 antibodies or antibody fragments, anti-CD150 antibodies or antibody fragments, anti-CD90 antibodies or antibody fragments, anti-CD27 antibodies or antibody fragments, anti-Esam antibodies or antibody fragments, anti-CD45 antibodies or antibody fragments, and any combination thereof.

The method can be performed with an HSC-depleting composition comprising a conjugate between an HSC-recognition molecule and a toxin. The HSC-recognition molecule of the conjugate may be selected from the group consisting of an antibody or antibody fragment, ligand and aptamer. The HSC-recognition molecule of the conjugate may be selected from the group consisting of: anti-CD117 antibody or antibody fragment, anti-CD110 antibody or antibody fragment, anti-CD201 antibody or antibody fragment, anti-CD150 antibody or antibody fragment, anti-CD90 antibody or antibody fragment, anti-CD27 antibody or antibody fragment, anti-Esam antibody or antibody fragment, anti-CD45 antibody or antibody fragment, and any combination thereof. A particularly preferred HSC-recognition molecule of the conjugate is an anti-human CD117 antibody or antibody fragment.

The HSC-recognition molecule of the conjugate may be a ligand, wherein the ligand is a peptide which binds to a protein displayed at the cell surface of the patient's HSC, and wherein the protein is selected from the group consisting of CD117, CD110, CD201, CD150, CD90, CD27, Esam, and CD45. A particularly preferred peptide for the HSC-recognition molecule is c-Kit ligand or thrombopoietin. In some conjugates, a toxin is chemically coupled to the HSC cell-recognition molecule. Other conjugates are recombinant fusion molecule in which the toxin is fused in frame with the HSC-recognition molecule. Toxins include a ribosome-inactivating protein (RIP). Toxins also include any of the following: saporins, saporin derivatives, ricin, abrin, gelonin, momordin, apitoxin, shiga toxins, shiga-like toxins, T-2 mycotoxin, diphtheria toxin, and busulfan.

Suitable donors include a HLA-mismatched donor who differs from a recipient patient in one or more alleles selected from the group consisting of: HLA-A locus, HLA-B locus, HLA-C locus, HLA-DRB1 locus, HLA-DQ locus, and any combination thereof.

Suitable immunosuppressive drugs include rapamycin, sirolimus, tacrolimus, cyclosporine, prednisone, and any combination thereof. Suitable T-cell depleting or inhibiting antibody or antibody fragment includes CD3 antibody or antibody fragment, CD4 antibody or antibody fragment, CD52 antibody or antibody fragment, ICOS antibody or antibody fragment, CD40 ligand antibody or antibody fragment, CD8 antibody or antibody fragment, antithymocyte globulin (ATG) and any combination thereof.

Also provided is a method of treating a hematological disorder selected from the group consisting of leukemia, lymphoma, myeloma, and hereditary or acquired immunodeficiency, hemoglobinopathy, fanconi anemia, post-transplant lymphoproliferative disease (PTLD). In this method, a patient is first administered an HSC-depleting composition. The patient is then optionally immunosuppressed by administering a medicament selected from the group consisting of a T-cell depleting or inhibiting antibody or antibody fragment, NK-cell depleting or inhibiting antibody or antibody fragment, an immunosuppressive drug, and any combination thereof. The patient is then treated with allogeneic cells selected from bone marrow cells, umbilical cord blood cells, hematopoietic stem and progenitor cells (HSPCs), peripheral blood CD34 cells, peripheral blood $CD34^+$ and $CD90^+$ cells, and any combination thereof. The HSC-depleting composition comprises a compound selected from the group consisting of: an antibody or antibody fragment with specific binding affinity to a protein displayed at the HSC surface, a conjugate comprising an HSC-recognition molecule and a toxin, and any combination thereof.

Also provided is a method of treating a patient where the method comprises the following steps: 1) administering to the patient an HSC-depleting composition; 2) administering to the patient allogeneic cells selected from the group consisting of bone marrow cells, umbilical cord blood cells, hematopoietic stem and progenitor cells (HSPCs), peripheral blood $CD34^+$ cells, and peripheral blood $CD34^+$ and $CD90^+$ cells, and any combination thereof; 3) grafting a transplant from the HLA-mismatched donor to the patient; and 4) optionally administering to the patient a medicament selected from the group consisting of a T-cell depleting or inhibiting antibody or antibody fragment, NK-cell depleting or inhibiting antibody or antibody fragment, an immunosuppressive drug, and any combination thereof. The medicament is administered during a time period selected from the group consisting of: prior to the administration of the HSC-depleting composition; during administration of the HSC-depleting composition; after the administration of the HSC-depleting composition, but before the administration of the allogeneic cells; during administration of the allogeneic cells; after the administration of the allogeneic cells, but before the transplant grafting; during the transplant grafting; after the transplant grafting; and any combination thereof. The HSC-depleting composition comprises a compound selected from the group consisting of: an antibody or antibody fragment with specific binding affinity to a protein displayed at the HSC surface, a conjugate comprising an HSC-recognition molecule and a toxin, and any combination thereof. The transplant is selected from the group consisting of kidney, skin, liver, heart, lung, bone marrow, hair follicles, muscle, ligament, nerve, tendon, bone, limb, face, abdominal wall, eye, ear, retina, hematopoietic stem cells, induced pluripotent stem cells (iPSCs), cells derived from iPSCs, bone marrow cells, islet cells, neurons, hematopoietic cells, epithelial cells, hepatocytes, cardiomyocytes, keratinocytes, and any combination thereof. This method includes patients who are treated for a disease selected from the group consisting of cancer, type I diabetes, multiple sclerosis, Parkinson disease, Alzheimer's disease, spinal cord injury, and ulcerative colitis. Patients in need of skin grafts, including burn victims, may be treated by this method as well.

Also provided is a method of treating a patient with a recombinant composition, in which the patient is administered an HSC-depleting composition; gene-modified autologous HSCs tolerant to the recombinant formulation; and the recombinant formulation. The patient is also optionally administered a medicament selected from the group consisting of a T-cell depleting or inhibiting antibody or antibody fragment, natural killer (NK) cell depleting or inhibiting antibody or fragment, immunosuppressive drug, and any combination thereof, wherein the medicament is administered during a time period selected from the group consisting of: prior to the administration of the HSC-depleting composition; during administration of the HSC-depleting composition; after the administration of the HSC-depleting composition, but before the administration of the gene-modified autologous HSCs; during administration of the gene-modified autologous HSCs; after the administration of the gene-modified autologous HSCs; after the administration of the recombinant formulation; and any combination thereof. The HSC-depleting composition comprises a compound selected from the group consisting of: an antibody or antibody fragment with specific binding affinity to a protein displayed at the HSC surface, a conjugate comprising an HSC-recognition molecule and a toxin, and any combination thereof. The recombinant formulation may comprise a recombinant adeno-associated virus (AAV), adenovirus, factor VIII, or factor IX.

Further provided is a method of tolerizing a patient to a recombinant formulation. The method comprises: first administering to the patient an HSC-depleting composition; then administering to the patient gene-modified autologous HSCs that give rise to cells which are tolerant to the recombinant formulation; and further optionally administering to the patient the recombinant formulation; and optionally administering to the patient a medicament selected from the group consisting of a T-cell depleting or inhibiting antibody or antibody fragment, natural killer (NK) cell depleting or inhibiting antibody or fragment, immunosuppressive drug, and any combination thereof, wherein the medicament is administered during a time period selected from the group consisting of: prior to the administration of the HSC-depleting composition; during administration of the HSC-depleting composition; after the administration of the HSC-depleting composition, but before the administration of the gene-modified autologous HSCs; during administration of the gene-modified autologous HSCs; after the administration of the gene-modified autologous HSCs; after the administration of the recombinant formulation; and any combination thereof. In this method, the HSC-depleting composition comprises a compound selected from the group consisting of: an antibody or antibody fragment with specific binding affinity to a protein displayed at the HSC surface, a conjugate comprising an HSC-recognition molecule and a toxin, and any combination thereof. The recombinant formulation may comprise a recombinant adeno-associated virus (AAV), adenovirus, factor VIII, and/or factor IX.

Further provided is a method of treating a patient for an autoimmune disease, in which a patient is administered an HSC-depleting composition; administered allogeneic cells selected from the group consisting of allogeneic cells selected from bone marrow cells, umbilical cord blood cells, hematopoietic stem and progenitor cells (HSPCs), peripheral blood $CD34^+$ cells, peripheral blood $CD34^+$ and $CD90^+$ cells, and any combination thereof; and optionally also administered a medicament selected from the group consisting of a T-cell depleting or inhibiting antibody or antibody fragment, NK-cell depleting or inhibiting antibody or fragment, immunosuppressive drug, and any combination thereof, wherein the medicament is administered during a time period selected from the group consisting of: prior to the administration of the HSC-depleting composition; during administration of the HSC-depleting composition; after the administration of the HSC-depleting composition, but before the administration of the allogeneic cells; during administration of the allogeneic cells; after the administration of the allogeneic cells; and any combination thereof. The HSC-depleting composition comprises a compound selected from the group consisting of: an antibody or antibody fragment with specific binding affinity to a protein displayed at the HSC surface, a conjugate comprising an HSC-recognition molecule and a toxin, and any combination thereof. The autoimmune disease is selected from the group consisting of diabetes mellitus type 1, Graves disease, inflammatory bowel disease, Crohn's disease, ulcerative colitis, multiple sclerosis, systemic sclerosis, psoriasis, rheumatoid arthritis, immune thrombocytic purpura, systemic lupus erythematosus, juvenile idiopathic arthritis, and autoimmune cytopenia.

Further embodiments provide a method of treating a patient for an autoimmune disease, in which the patient is administered an HSC-depleting composition; gene-modified autologous HSCs; and optionally also administered a medicament selected from the group consisting of a T-cell depleting or inhibiting antibody or antibody fragment, NK-cell depleting or inhibiting antibody or fragment, immunosuppressive drug, and any combination thereof, wherein the medicament is administered during a time period selected from the group consisting of: prior to the administration of the HSC-depleting composition; during administration of the HSC-depleting composition; after the administration of the HSC-depleting composition, but before the administration of the gene-modified autologous HSCs; during administration of the gene-modified autologous HSCs; after the administration of the gene-modified autologous HSCs; and any combination thereof. The HSC-depleting composition comprises a compound selected from the group consisting of: an antibody or antibody fragment with specific binding affinity to a protein displayed at the HSC surface, a conjugate comprising an HSC-recognition molecule and a toxin, and any combination thereof. The autoimmune disease is selected from the group consisting of diabetes mellitus type 1, Graves disease, inflammatory bowel disease, Crohn's disease, ulcerative colitis, multiple sclerosis, systemic sclerosis, psoriasis, rheumatoid arthritis, immune thrombocytic purpura, systemic lupus erythematosus, juvenile idiopathic arthritis, and autoimmune cytopenia. The gene-modified autologous HSCs may express an antigen selected from the group consisting of myelin or myelin fragment; and a protein marker expressed on the surface of islet cells.

DETAILED DESCRIPTION

Figure 1:
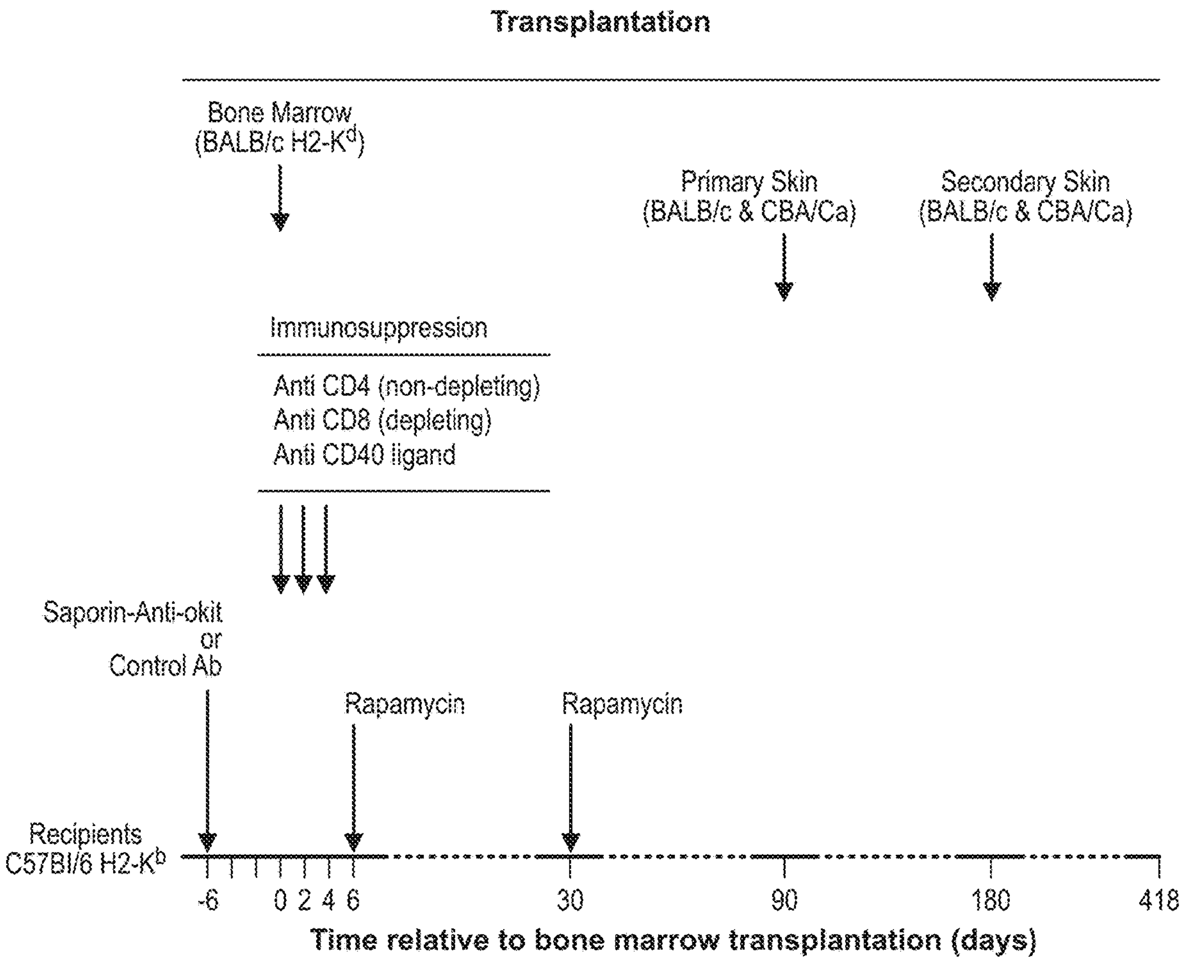
FIG. 1 is a protocol for an allogeneic skin engraftment study.

A method is provided for improving tolerance in a patient to an allogeneic transplant from a donor who is not an identical twin to the patient, including an HLA-mismatched donor, HLA-matched donor, HLA-partially matched donor, HLA-unmatched donor, and HLA-matched donor with minor mismatches. A method is also provided for increasing chimerism in a recipient of allogeneic bone marrow cells, umbilical cord blood cells or hematopoietic stem and progenitor cells from an HLA-mismatched donor.

The term "allogeneic transplant or graft" is used in this disclosure broadly to mean any transplant which is not genetically identical to a patient recipient. More specifically, any transplant from any donor who is not an identical twin to a patient recipient, is referred to as an allogeneic transplant as these transplants are not genetically identical to a patient recipient. The allogeneic transplants include those provided by an HLA-mismatched donor, HLA-matched donor who is not an identical twin to a patient, HLA-partially matched donor, HLA-unmatched donor who is not an identical twin to a patient, and HLA-matched donor with minor mismatches. Thus, the term "donor" of an allogeneic transplant means any donor who is not an identical twin to a patient recipient.

An allogeneic transplant includes any of the following allogeneic cells obtained from a donor who is not an identical twin to a recipient: bone marrow cells, umbilical cord blood cells, hematopoietic stem and progenitor cells (HSPC), peripheral blood $CD34^+$ cells, peripheral blood $CD34^+$ and $CD90^+$ cells, embryonic stem (ES) cells, and induced pluripotent stem cells (iPSCs).

An allogeneic transplant may further include any tissue and/or organ obtained from the same donor who has provided the allogeneic cells. Allogeneic transplant tissues and organs include, but are not limited to, kidney, skin, liver, heart, lung, bone marrow, hair follicles, muscle, ligament, nerve, tendon, bone, limb, face, abdominal wall, eye, ear, or retina. Further examples of allogeneic transplants include hematopoietic stem cells, induced pluripotent stem cells (iPSCs), cells derived from iPSCs, bone marrow cells, islet cells, neurons, hematopoietic cells, epithelial cells, hepatocytes, cardiomyocytes, keratinocytes, embryonic stem cells (ESCs), cells derived from ESCs, mesenchymal stem cells (MSCs), and cells derived from MSCs.

It will be further appreciated that the term "HLA-mismatched donor" is understood broadly and includes any donor who is not fully HLA-identical to a patient. The HLA-mismatched donor includes a partially-matched donor, including a donor who is identical to a patient in all, but one HLA-locus. An HLA-mismatched donor includes a donor who matches a patient in any 9 alleles from two HLA-A, two HLA-B, two HLA-C, two HLA-DRB1 loci, and two DQ alleles. An HLA-mismatched donor includes a donor who matches a patient in any 8 alleles from two HLA-A, two HLA-B, two HLA-C, two HLA-DRB1 loci, and two DQ alleles. An HLA-mismatched donor includes a donor who matches a patient in any 7 alleles from two HLA-A, two HLA-B, two HLA-C, two HLA-DRB 1 loci, and two DQ alleles. An HLA-mismatched donor includes a donor who matches a patient in any 6 alleles from two HLA-A, two HLA-B, two HLA-C, two HLA-DRB1 loci, and two DQ alleles. An HLA-mismatched donor includes a donor who matches a patient in any 6 alleles from two HLA-A, two HLA-B, two HLA-C, two HLA-DRB1 loci, and two DQ alleles. An HLA-mismatched donor includes a donor who matches a patient in any 5 alleles from two HLA-A, two HLA-B, two HLA-C, two HLA-DRB1 loci, and two DQ alleles. An HLA-mismatched donor includes a donor who matches a patient in any 4 alleles from two HLA-A, two HLA-B, two HLA-C, two HLA-DRB1 loci, and two DQ alleles. An HLA-mismatched donor includes a donor who matches a patient in any 3 alleles from two HLA-A, two HLA-B, two HLA-C, two HLA-DRB1 loci, and two DQ alleles. An HLA-mismatched donor includes a donor who matches a patient in any 2 alleles from two HLA-A, two HLA-B, two HLA-C, two HLA-DRB1 loci, and two DQ alleles. An HLA-mismatched donor includes a donor who matches a patient in any 1 allele from two HLA-A, two HLA-B, two HLA-C, two HLA-DRB1 loci, and two DQ alleles. An HLA-mismatched donor includes a donor who does not match a patient in any allele from two HLA-A, two HLA-B, two HLA-C, two HLA-DRB1 loci, and two DQ alleles. It will be further appreciated that a suitable HLA-mismatched donor also includes a donor who carries mismatches in some other HLA alleles, in addition or instead of the 10 alleles described above.

The term "minor mismatches" refers to genetic differences between a donor and a recipient in any locus other than the HLA-loci.

It will be further appreciated that the HLA-matching can be performed by using any one of standard HLA-typing methods, including the PCR-sequence-specific oligonucleotide (SSO) probing or the sequence-specific primer (SSP) technology, as described in detail in "HLA Typing by SSO and SSP methods" by Heather Dunckley (Series "Methods in Molecular Biology," 2012; Vol. 882; pp 9-25).

The present methods condition a patient recipient to tolerate an allogeneic transplant from any donor. Thus, the allogeneic grafting to the conditioned patient can be performed without the need for HLA-typing in some embodiments. The methods include HLA-unmatched donors for whom HLA-typing has not been performed.

The methods comprise depleting hematopoietic stem cells (HSCs) of a patient with an HSC-depleting composition, and administering to the patient allogeneic cells selected from bone marrow cells, umbilical cord blood cells, a population of hematopoietic stem and progenitor cells (HSPCs), peripheral blood $CD34^+$ cells, peripheral blood $CD34^+$ and $CD90^+$ cells, and any combination thereof.

Hematopoietic stem cells (HSCs) are the stem cells that give rise to all other blood cells through the process of hematopoiesis. During differentiation, the progeny of HSCs progresses through pluripotent, multi-potent and lineage-committed progenitor cells prior to reaching maturity and becoming fully differentiated blood cells.

An allogeneic transplant can be prepared by obtaining bone marrow or umbilical cord blood cells from a donor who is not an identical twin to a patient. In some embodiments of the method, the population of CD34+ and CD34+CD90+ cells can then be purified from the bone marrow, umbilical cord blood cells, or peripheral blood cells by any of the conventional methods, such as for example, a fluorescent cell sorting (FACS sorting) of CD34+ and CD34+CD90+ cells. This population of cells enriched in CD34+ and CD34+CD90+ cells can be used as an allogeneic transplant in some embodiments.

The method may also further comprise treating the patient with a medicament selected from an immunosuppressive drug, T-cell depleting or inhibiting antibody or antibody fragment, Natural Killer (NK)-depleting or inhibiting antibody or antibody fragment, and any combination thereof in order to stimulate immunosuppression in the patient. This immunosuppressive treatment may be performed at any time, including before or after a treatment with an HSC-depleting composition, and/or before or after the administration of allogeneic cells selected from bone marrow cells, umbilical cord blood cells, hematopoietic stem and progenitor cells (HSPC), peripheral blood $CD34^+$ cells, peripheral blood $CD34^+$ and $CD90^+$ cells. The immunosuppressive treatment can be repeated as many times as needed, and may be continued after the administration of the allogeneic cells for a period of time.

The term "immunosuppressive drug" includes any drug that suppresses, or inhibits, the strength of the patient's immunes system. Immunosuppressive drugs include glucocorticoids, cytostatics, antibodies, drugs that act on immunophilins, interferons, mycophenolates and antimetabolites. Immunosuppressive drugs include rapamycin and rapamycin derivatives, including sirolimus, tacrolimus; and evarolimus. Other immunosuppressive drugs include azathioprine, mycophenolate; cyclosporine, dactinomycin, anthracyclines, mitomycin C, bleomycin, mithramycin, methotrexate, fluorouracil, cyclophosphamide, prednisone and any combination thereof. Antibodies includes heterologous polyclonal antibodies and monoclonal antibodies. Heterologous polyclonal antibodies can be obtained from the serum of an animal injected with the patient's thymocytes or lymphocytes. The resulting polyclonal preparation, such as the antilymphocyte (ALG) and antithymocyte globulin (ATG) can be used as an immunosuppressive drug. Monoclonal antibodies include T-cell receptor directed antibodies and antibody fragments which deplete or inhibit T cells. Monoclonal antibodies also include antibodies or antibody fragments that deplete or inhibit NK-cells. Monoclonal antibodies also include IL-2 receptor directed antibodies.

T-cell depleting or inhibiting antibodies include CD3 antibody or antibody fragment, CD4 antibody or antibody fragment, CD52 antibody or antibody fragment, ICOS antibody or antibody fragment, CD40 ligand antibody or antibody fragment, CD8 antibody or antibody fragment, polyclonal antithymocyte globulin (ATG), and any combination thereof. Some of these antibodies such as CD52 and CD40 ligand antibody also deplete or inhibit NK (natural killer) cells.

The method may further comprise treating the allogeneic transplant with a T-cell depleting or inhibiting agent, such as antibody or antibody fragment, prior to the administration to the patient.

According to the present methods, the depletion of hematopoietic stem cells is carried out by administering to a patient an HSC-depleting composition which triggers depletion of hematopoietic stem cells. At least in some applications, the HSC-depleting composition may cause cell-cycle arrest, differentiation, apoptosis, cytolysis or phagocytosis of hematopoietic stem cells.

The depletion of hematopoietic stem cells can be carried out by administering to a patient an HSC-depleting composition comprising an antibody or antibody fragment with specific binding affinity to the patient's hematopoietic stem cells. Suitable antibodies or antibody fragments include those which recognize and bind a protein displayed at the cell surface of a patient's hematopoietic stem cell.

These antibodies or antibody fragments include an antibody or antibody fragment with specific binding affinity to at least one of the following human proteins: CD117, CD110, CD201, CD150, CD90, CD27, Esam, and CD45. The contemplated antibodies or antibody fragments include monoclonal antibodies and antibody fragments with specific binding affinity to a protein (or protein fragment) selected from human CD117, human CD110, human CD201, human CD150, human CD90, human CD27, human Esam, and human CD45. Particularly preferred are humanized monoclonal antibodies or antibody fragments with specific binding affinity to a protein (or protein fragment) selected from human CD117, human CD110, human CD201, human CD150, human CD90, human CD27, human Esam, and human CD45. These antibodies or antibody fragments selectively recognize and bind to an extracellular domain of at least one of these proteins displayed at the cell surface of a human HSC.

The term specific binding affinity is understood broadly and includes any antibody or antibody fragment with $K_d$ (the equilibrium dissociation constant between the antibody or antibody fragment and its antigen) in the range from $10^{-6}$ M to $10^{-12}$ M. Particularly preferred antibodies or antibody fragments include those with $K_d$ in the range from $10^{-9}$ M to $10^{-12}$ M.

It will be appreciated that the term "antibody or antibody fragment" is to be understood broadly and includes all five immunoglobulin (Ig) classes: IgG, IgM, IgA, IgE and IgD. The term "antibody or antibody fragment" also includes monoclonal antibodies, single chain antibodies, complementarity-determining regions (CDRs), an antigen-binding fragment (Fab), an antibody fragment in which two antigen-binding fragments are linked together by disulfide bonds ($F(ab)_2$), single chain variable fragment (scFv) and a diabody composed of non-covalent dimers of scFvs. Particularly preferred are antigen-binding fragments selected from the following group: anti-CD117 humanized Fab, anti-CD110 humanized Fab, anti-CD201 Fab, anti-CD150 humanized Fab, anti-CD90 humanized Fab, anti-CD27 humanized Fab, anti-Esam humanized Fab, and anti-CD45 humanized Fab.

An antibody or antibody fragment may be obtained by a hybridoma technique, for example as described in (Kozbor et al., 1983, Immunology Today, 4:72) or (Cole et al., Monoclonal Antibodies and Cancer Therapy, pp 77-96, Alan R Liss, Inc., 1985). As an alternative, an antibody or antibody fragment can be obtained by a recombinant procedure, such as for example, by screening a cDNA library of immunoglobulin variable regions, for example as described in WO 1992/002551. An antibody or antibody fragment can be pegylated or otherwise modified, for example by deleting at least a portion of an antibody, replacing at least one amino acid, inserting a linker sequence, and engineering a chimeric antibody which simultaneously recognizes two different antigens.

One particularly preferred HSC-depleting composition comprises anti-human CD117 antibody or antibody fragment. CD117 is a 145 kDa immunoglobulin superfamily member also known as c-Kit, steel factor receptor and stem cell factor receptor (SCFR). It is a transmembrane tyrosine-kinase receptor that binds the c-Kit ligand (also known as steel factor, stem cell factor, and mast cell growth factor).

An HSC-depleting composition comprising at least one antibody or antibody fragment selected from anti-human CD117, anti-human CD110, anti-human CD201, anti-human CD150, anti-human CD90, anti-human CD27, anti-human Esam, and anti-human CD45 antibodies or antibody fragments, can be administered to a patient in an amount from 0.01 mg/kg to 50 mg/kg. The preferred method of administration for the HSC-depleting composition is intravenous (i.v.). In some embodiments, the HSC-depleting composition can be administered to a patient at least one day, at least two days, at least 3 days, at least 4 days, at least 5 days, at least 6 days, at least 7 days, at least 8 days, at least 9 days, at least 10 days, at least 11 days, at least 12 days, at least 13 days, or at least 14 days prior to administering to the patient allogeneic cells selected from bone marrow cells, umbilical cord blood cells, hematopoietic stem and progenitor cells (HSPC), peripheral blood $CD34^+$ cells, peripheral blood $CD34^+$ and $CD90^+$ cells, and any combination thereof. The composition can be administered at least once. The patient can be monitored for depletion of HSCs post-administration. If needed, the treatment with the HSC-depleting composition can be repeated as many times as needed.

It will be appreciated that the term depletion of HSCs means a decrease in the number of viable functional HSCs in comparison to the number of viable functional HSCs prior to the administration of the HSC-depleting composition. Any decrease in the number of viable functional HSCs is considered to be a depletion of HSCs. This includes a decrease in the number of viable functional HSCs in the range from 5% to 20%, from 5% to 30%, from 5% to 40%, from 5% to 50%, from 5% to 60%, from 5% to 70%, from 5% to 80%, from 5% to 90%, and from 5% to 100%, as compared to the number of viable functional HSCs before treatment with the HSC-depleting composition.

Other HSC-depleting compositions may comprise a conjugate comprising an HSC-recognition molecule and a toxin. Suitable HSC-recognition molecules include an antibody or antibody fragment with specific binding to a protein displayed at the surface of human hematopoietic stem cells. In particular, suitable HSC-recognition molecules include any of the antibodies or antibody fragments as described in connection with the HSC-depleting compositions comprising an antibody or antibody fragment.

At least in some embodiments, the HSC-recognition molecule is selected from anti-CD117 antibodies or antibody fragments, anti-CD110 antibodies or antibody fragments, anti-CD201 antibodies or antibody fragments, anti-CD150 antibodies or antibody fragments, anti-CD90 antibodies or antibody fragments, anti-CD27 antibodies or antibody fragments, anti-Esam antibodies or antibody fragments, anti-CD45 antibodies or antibody fragments, and any combination thereof. An anti-human CD117 antibody or antibody fragment is particularly preferred as an HSC-recognition molecule.

In further embodiments, the HSC-recognition molecule can be a ligand with specific binding to at least one protein displayed at the surface of a human hematopoietic stem cell. Suitable ligands include peptides which specifically recognize and bind to a protein displayed at the surface of a human HSC. Such proteins include CD117, CD110, CD201, CD150, CD90, CD27, Esam, and CD45. Suitable ligands include native ligands such as for example stem cell factor (SCF, KIT-ligand, KL or steel factor) and thrombopoietin (TRO). Suitable ligands also include recombinant peptides engineered to interact with an extracellular domain of a protein selected from human CD117, CD110, CD201, CD150, CD90, CD27, Esam, CD45, and any combination thereof. A particularly preferred ligand is KIT-ligand. In further embodiments, KIT-ligand which can be further modified by deletion, insertion and/or replacement of at least some of the amino acids.

In further embodiments, the HSC-recognition molecule can be an aptamer (ssDNA or ssRNA) with specific binding to at least one protein displayed at the surface of a human hematopoietic stem cell. Suitable aptamers include those which bind to an extracellular domain of at least one of the following human proteins: CD117, CD110, CD201, CD150, CD90, CD27, Esam, and CD45. Particularly preferred are aptamers specific to human CD117 protein.

When an HSC-depleting composition is a conjugate, it comprises a toxin in addition to an HSC-recognition molecule. The toxin can be chemically coupled to the HSC-recognition molecule, including by a covalent or non-covalent bond, or through a linker. At least in some embodiments, the linker may comprise two molecules, a first molecule being linked to a HSC-recognition molecule, and a second molecule being linked to a toxin. The first molecule and second molecules have a binding affinity to each other and complex together when mixed. The complex between the first molecule and the second molecule links the HSC cell-recognition molecule to the toxin. A suitable two-molecule linker includes biotin and streptavidin. In at least one embodiment, an HSC-recognition molecule is coupled with biotin. A toxin is then coupled with streptavidin. When mixed together, biotin complexes with streptavidin and the complex links the HSC-recognition molecule to the toxin. In other embodiments, an HSC-recognition molecule is coupled with streptavidin. A toxin is then coupled with biotin. When mixed together, biotin complexes with streptavidin and the complex links the HSC-recognition molecule to the toxin.

Suitable conjugates can be prepared with a toxin selected from a peptide, protein or small organic molecule which triggers a cell death and/or cell cycle arrest in human hematopoietic stem cells. Such toxins include ribosome-inactivating proteins (RIP) which irreversibly inactivate protein synthesis. Plant-derived toxins include saporins, ricin and abrin. Bacteria-derived toxins include Shiga toxins. Suitable toxins include saporins and saporin derivatives, ricin, abrin, gelonin, momordin, apitoxin, Shiga toxins, Shiga-like toxins, and T-2 mycotoxin. Modified saporins, ricin, abrin, gelonin, momordin, apitoxin, Shiga toxins, Shiga-like toxins, and T-2 mycotoxin are contemplated as well.

Additional suitable toxins include those described in WO 2016/164502, including diphtheria toxin, pseudomonas exotoxin A, Ricin A chain derivatives, abrin, modeccin, gelonin, momordin, trichosanthin, luffin toxin and any combinations thereof. Suitable toxins also include one or more DNA-damaging molecules, one or more anti-tubulin agents (e.g. maytansines) or tubulin inhibitors, one or more amatoxins or a functional fragment, derivative or analog thereof. For example, contemplated toxins for use in accordance with any of the methods or compositions disclosed herein may include or comprise one or more amatoxins selected from the group consisting of a-amanitin, β-amanitin, γ-amanitin, £-amanitin, amanin, amaninamide, amanullin, amanullinic acid and any functional fragments, derivatives or analogs thereof.

A toxin can be a small organic molecule, including small molecules described in WO 2016/164745, including mechlorethamine, cyclophosphamide, ifosfamide, melphalan (1-sarcolysin), chlorambucil), ethylenimines and methylmelamines (e.g. altretamine (hexamethylmelamine; HMM), thiotepa (Methylene thiophosphoramide), triethylenemelamine (TEM)), alkyl sulfonates (e.g. busulfan), nitrosureas (e.g. carmustine (BCNU), lomustine (CCMU), semustine (methyl-CCNU), streptozocin (streptozotocin)), and triazenes (e.g. dacarbazine (DTIC; dimethyltriazenoimidazolecarboxamide)), methotrexate (amethopterin), fluorouracil (5-fluorouracil; 5-FU), floxuridine (fluorodeoxyuridine; FUdR), cytarabine (cytosine arabinoside), mercaptopurine (6-mercaptopurine; 6-MP), azathioprine, thioguanine (6-thioguanine; TG), fludarabine phosphate, pentostatin (2'-deoxycofonycin), and cladribine (2-chlorodeoxyadenosine; 2-CdA).

An HSC-depleting composition comprising a conjugate comprising an HSC-recognition molecule conjugated with a toxin can be administered to a patient in an amount from 0.01 mg/kg to 50 mg/kg. The preferred method of administration for the HSC-depleting composition is intravenous (i.v.). In some embodiments, the HSC-depleting composition can be administered to a patient at least one day, at least two days, at least 3 days, at least 4 days, at least 5 days, at least 6 days, at least 7 days, at least 8 days, at least 9 days, at least 10 days, at least 11 days, at least 12 days, at least 13 days, or at least 14 days prior to administering to the patient bone marrow cells, umbilical cord blood cells, or hematopoietic stem and progenitor cells obtained from a donor. The composition can be administered at least once. The patient can be monitored for depletion of HSCs post-administration. If needed, the treatment with the HSC-depleting composition can be repeated as many times as needed.

One of the preferred conjugates, referred hereafter as CD117-SAP, comprises an anti-human CD117 antibody or antibody fragment conjugated with saporin, such as for example saporin-6 (SAP6), or a saporin derivative. Suitable saporin derivatives include a modified peptide for SAP6. Suitable modifications may include deletions, insertions and point mutations in a coding sequence for SAP6. Suitable modifications may also include glycosylation of SAP6 peptide. CD117-SAP can be obtained by conjugating saporin or a saporin derivative to an anti-human CD117 antibody or antibody fragment by protocols provided in U.S. Pat. No. 7,741,435.

The CD117-SAP composition can be administered to a patient in an amount in the range from 0.01 milligram (mg) per one kilogram (kg) of patient's body weight (0.01 mg/kg) to 50 mg per one kg of patient's body weight (50 mg/kg). The preferred method of administration for the CD117-SAP composition is intravenous (i.v.). In some embodiments, the CD117-SAP composition can be administered to a patient at least one day, at least two days, at least 3 days, at least 4 days, at least 5 days, at least 6 days, at least 7 days, at least 8 days, at least 9 days, at least 10 days, at least 11 days, at least 12 days, at least 13 days, or at least 14 days prior to administering to the patient bone marrow cells, umbilical cord blood cells, or hematopoietic stem and progenitor cells obtained from a donor. The CD117-SAP composition can be administered at least once. The patient can be monitored for depletion of HSCs post-administration of the CD117-SAP composition. The treatment with the CD117-SAP composition can be repeated as many times as needed.

After a patient is treated with an HSC-depleting composition, the patient is infused with allogeneic cells selected from bone marrow cells, umbilical cord blood cells, hematopoietic stem and progenitor cells (HSPCs), peripheral blood $CD34^+$ cells, peripheral blood $CD34^+$ and $CD90^+$ cells, and any combination thereof. In some embodiments, the allogeneic cells comprise an enriched population of CD34+ and CD34+CD90+ cells obtained from bone marrow, umbilical cord blood cells or peripheral blood. One enrichment method that can be used is flow cytometry, for example as described in Tian et al. Ann Hematol. 2016, March, 95(4): 543-7.

It will be readily appreciated that while in the prior art, the preferred donor is an HLA-matched donor when no identical twin is available, unexpectedly, any donor, including an HLA-mismatched donor, is suitable for the present infusion method.

This result is highly unexpected because HSC transplants in prior art preferably require a match in eight MHC alleles (two HLA-A, two HLA-B, two HLA-C, and two HLA-DRB1 loci), with a mismatch in even one out of the 8 alleles decreasing a chance for successful transplantation significantly, according to the prior art methods.

In one embodiment of the present method, a patient is infused with bone marrow cells. A variable number of donor bone marrow cells can be infused. At least in some applications, a patient can be infused with a high dosage of HLA-mismatched donor bone marrow cells. At least in some treatment methods, a patient can receive at least 50,000 mln donor bone marrow cells; at least 100,000 mln donor bone marrow cells, or at least 500,000 mln donor bone marrow cells.

An allogeneic transplant may be pre-treated prior to infusion into a patient. In some embodiments, the allogeneic transplant is treated to deplete and/or inactivate T cells and/or natural killer (NK) cells prior to infusion into a patient. The depletion/inhibition of T and NK cells can be carried out by incubating the allogeneic transplant with an agent which can be an antibody or antibody fragment selected from anti-human CD3 antibody or antibody fragment, anti-human CD4 antibody or antibody fragment, anti-human CD52 antibody or antibody fragment, anti-human ICOS antibody or antibody fragment, anti-human CD40 ligand antibody or antibody fragment, anti-human CD8 antibody or antibody fragment, antithymocyte globulin (ATG, a lymphocyte-depleting polyclonal IgG preparation with specificity toward human thymocytes), and any combination thereof.

Some embodiments of the present method, a patient can be treated with a medicament selected from a T-cell depleting or inhibiting antibody or antibody fragment, natural killer (NK) cell depleting or inhibiting antibody or fragment, immunosuppressive drug, and any combination thereof. This treatment can take place prior to the administration of an HSC-depleting composition; during administration of the HSC-depleting composition; after the administration of the HSC-depleting composition, but before the administration of allogeneic cells selected from the group consisting of bone marrow cells, umbilical cord blood cells, hematopoietic stem and progenitor cells (HSPC), peripheral blood $CD34^+$ cells, peripheral blood $CD34^+$ and $CD90^+$ cells, and any combination thereof; during administration of the allogeneic cells; and/or after the administration of the allogeneic cells. The treatment can be repeated as many times as need.

In some embodiments, a patient is treated prior to administering allogeneic cells selected from the group consisting of bone marrow cells, umbilical cord blood cells, hematopoietic stem and progenitor cells (HSPC), peripheral blood $CD34^+$ cells, peripheral blood $CD34^+$ and $CD90^+$ cells, with at least one of the following medicaments: a T-cell depleting or inhibiting antibody or antibody fragment, natural killer (NK) cell depleting or inhibiting antibody or fragment, and an immunosuppressive drug. The patient can be also treated with at least one immunosuppressive drug after the administration of the allogeneic cells for a period of time in order to induce transient immunosuppression.

A patient can be treated with any of the following immunosuppressive drugs or any combination of the following immunosuppressive drugs: glucocorticoids, cytostatics, antibodies, drugs that act on immunophilins, interferons, mycophenolates and antimetabolites. Immunosuppressive drugs include rapamycin and rapamycin derivatives, including sirolimus, tacrolimus; and evarolimus. Other immunosuppressive drugs include azathioprine, mycophenolate; cyclosporine, dactinomycin, anthracyclines, mitomycin C, bleomycin, mithramycin, methotrexate, fluorouracil, cyclophosphamide, prednisone and any combination thereof. Antibodies includes heterologous polyclonal antibodies and monoclonal antibodies. Heterologous polyclonal antibodies include the antilymphocyte (ALG) and antithymocyte globulin (ATG). Monoclonal antibodies include T-cell receptor directed antibodies and antibody fragments which deplete or inhibit T cells. Monoclonal antibodies also include antibodies or antibody fragments that deplete or inhibit NK-cells. Monoclonal antibodies also include IL-2 receptor directed antibodies. The patient is treated with the immunosuppressive drugs and their combinations before the administration of the HSC-depleting composition, after the administration of the HSC-depleting composition, but before the administration of the allogeneic cells (selected from the group consisting of bone marrow cells, umbilical cord blood cells, hematopoietic stem and progenitor cells (HSPC), peripheral blood $CD34^+$ cells, peripheral blood $CD34^+$ and $CD90^+$ cells, and any combination thereof), during the administration of the allogeneic cells, and/or after the administration of the allogeneic cells. An immunosuppressive drug can be administered as a tablet, capsule, liquid and/or in injectable form. At least in some embodiments, the immunosuppressive drug can be injected in an amount from 1 mg/kg to 20 mg/kg per one administration cycle.

It will be appreciated that at least in some embodiments, the depletion and inhibition of T-cells and NK-cells can be carried out with a combination of depleting antibodies and inhibiting antibodies. At least one preferred combination comprises at least one depleting antibody and at least one inhibiting antibody. A T-cell depleting antibody can be selected from anti-human CD3 antibody or antibody fragment, anti-human CD4 antibody or antibody fragment, anti-human CD52 antibody or antibody fragment, anti-human ICOS antibody or antibody fragment, anti-human CD40 ligand antibody or antibody fragment, anti-human CD8 antibody or antibody fragment. A T-cell non-depleting (inhibiting) antibody can be selected from the group consisting of human CD3 antibody or antibody fragment, anti-human CD4 antibody or antibody fragment, anti-human CD52 antibody or antibody fragment, anti-human ICOS antibody or antibody fragment, anti-human CD40 ligand antibody or antibody fragment. In some embodiments, a patient is treated with a composition comprising, consisting essentially of, or consisting of at least one CD4 antibody, at least one CD8 antibody and at least one CD40 ligand antibody. In other embodiments, a patient is treated with a medicament comprising at least one of the following CD52, CD40 ligand, and ATG.

In some embodiments, depletion of T-cells is carried out prior to a bone marrow transplant into a patient. In other embodiments, T-cell depletion can be carried out simultaneously with infusion into a patient. Yet in other embodiments, a patient can be treated with a T-cell depleting agent or a combination thereof after the patient has been infused with bone marrow cells and/or HSPCs. Suitable T-cell depleting agents and compositions include CD3 antibody or antibody fragment, CD4 antibody or antibody fragment, CD52 antibody or antibody fragment, ICOS antibody or antibody fragment, CD40 ligand antibody or antibody fragment, CD8 antibody or antibody fragment, and any compositions thereof. A particularly preferred T-cell depleting composition comprises, consisting essentially of, or consisting of at least one CD4 antibody, at least one CD8 antibody and at least one CD40 ligand antibody.

In other embodiments, a patient is not treated with an immunosuppressive drug or the patient is treated with an immunosuppressive drug only for a short period of time needed to prevent an acute rejection. Thus, the present methods may provide a significant technical advantage over prior art engraftment methods where a patient is often required to take an immunosuppressive drug for life. In the present methods, an administration period for an immunosuppressive drug may be shorter and/or the effective dosage of the immunosuppressive drug may be decreased in comparison to conventional transplant methods performed without an HSC-depleting composition. At least in some embodiments, an immunosuppressive drug can be avoided all together.

Various technical advantages are provided by the present conditioning and infusion method. It has been unexpectedly discovered that the present method with an HSC-depleting composition and transient immunosuppression conditions a recipient such that the recipient becomes tolerant to allogeneic cells selected from bone marrow cells, umbilical cord blood cells, hematopoietic stem and progenitor cells (HSPC), peripheral blood $CD34^+$ cells, peripheral blood $CD34^+$ and $CD90^+$ cells, and derived from a donor who is not an identical twin for the patient, including from an HLA-mismatched donor.

A significantly improved level of chimerism has been observed for these recipients in comparison to recipients who have been infused with bone marrow or HSCs from an HLA-mismatched donor without depleting HSCs of a recipient with an HSC-depleting composition. In the present method with an HSC-depleting composition, at least 1.5% to 2% of blood cells in the recipient after the infusion represent HSCs originating from the HLA-mismatched donor. In some embodiments, at least 2.0% to 20% of blood cells in the recipient after the infusion represent HSCs originating from the HLA-mismatched donor. The high level of chimerism is detected for a long period of time post-infusion. At least in some embodiments, at least 2% to 20% of recipient blood cells derive from the donor HSCs when measured 3 to 6 months after the infusion.

The improved tolerance by a recipient of HLA-mismatched HSCs and the increase in chimerism with contribution from HLA-mismatched HSCs opens the opportunity to employ the present method for treating patients in need of an allogeneic HSC transplant (AHSCT). The present methods safely establish robust hematopoietic chimerism without toxic conditioning in an allogeneic setting by using an HSC-depleting composition with transient immunosuppression.

FIG. 1 is an allogeneic transplant treatment protocol. Day zero is a day on which a recipient receives allogeneic bone marrow. The recipient is treated with an HSC-depleting composition several days prior to the allogeneic bone marrow transplant. The recipient is also transiently immunosuppressed with a combination of T-cell depleting and inhibiting antibodies soon after receiving the allogeneic bone marrow transplant. The recipient also receives at least two dosages of immunosuppressive drug rapamycin on the schedule shown in FIG. 1. The recipient then receives a primary and secondary skin grafts on schedule as shown in FIG. 1.

Figure 2A:
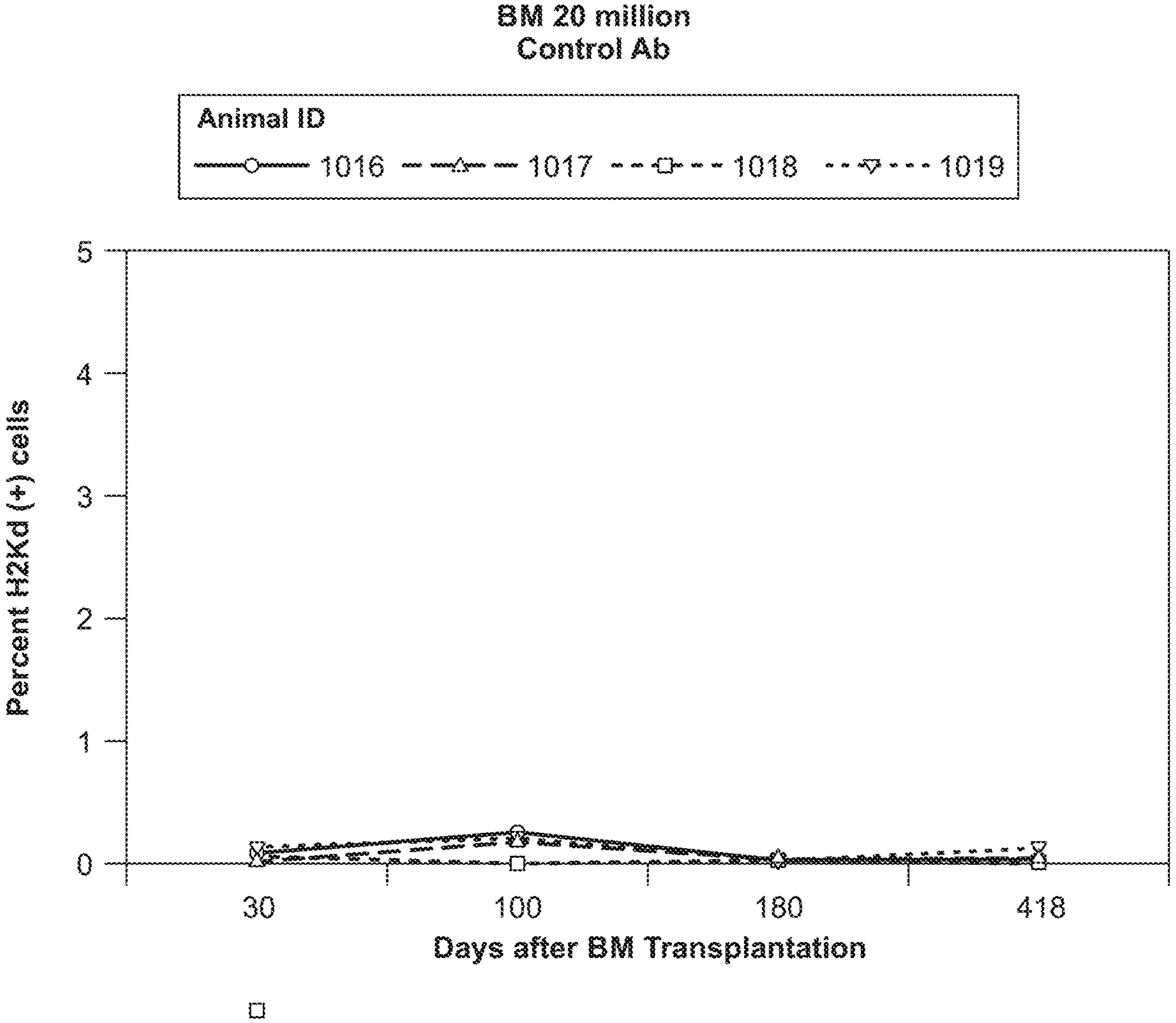
FIGS. 2A and 2B report mixed chimerism levels in blood of recipients conditioned with a control antibody and infused with allogeneic bone marrow cells (FIG. 2A) versus recipients conditioned with CD117-SAP and infused with allogeneic bone marrow cells (FIG. 2B).
Figure 2B:
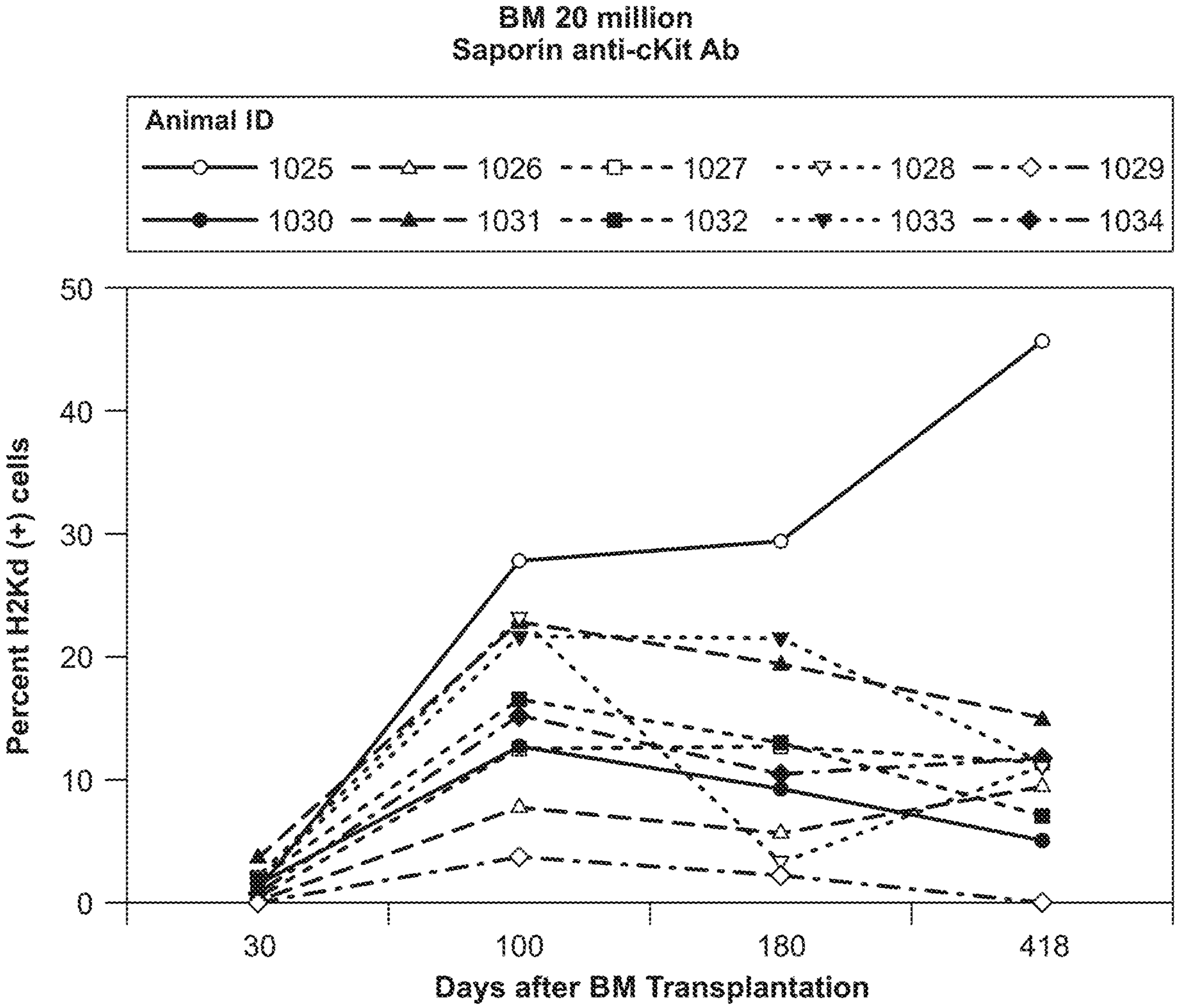

FIGS. 2A and 2B report improved chimerism in recipients of HLA-mismatched bone marrow infusion. The recipients in FIG. 2B were administered an HSC-depleting composition, and infused with allogeneic bone marrow cells. Prior to the infusion, the recipients were also transiently treated with T-cell depleting agents and an immunosuppressive drug. See FIG. 1 for the treatment protocol details. The control group in FIG. 2A was treated with a control immunoglobulin with no antigenic specificity instead of the HSC-depleting composition, but otherwise was treated the same.

The X axis in graphs of FIGS. 2A and 2B stands for the days after allogeneic bone marrow transplantation. The numbers on Y axis are the percentage of mononuclear cells that express Balb/c MHC class I (H2Kd) in total mononuclear cells of the peripheral blood in the recipient. These cells are believed to be donor-derived since H2Kd is only found on Balb/c, but not C57Bl/6 cells. In comparing FIG. 2A to FIG. 2B, conditioning with an HSC-depleting composition improves chimerism in recipients of HLA-mismatched bone marrow. This result is further highlighted in a comparative chart of FIG. 2C.

Figure 3A:
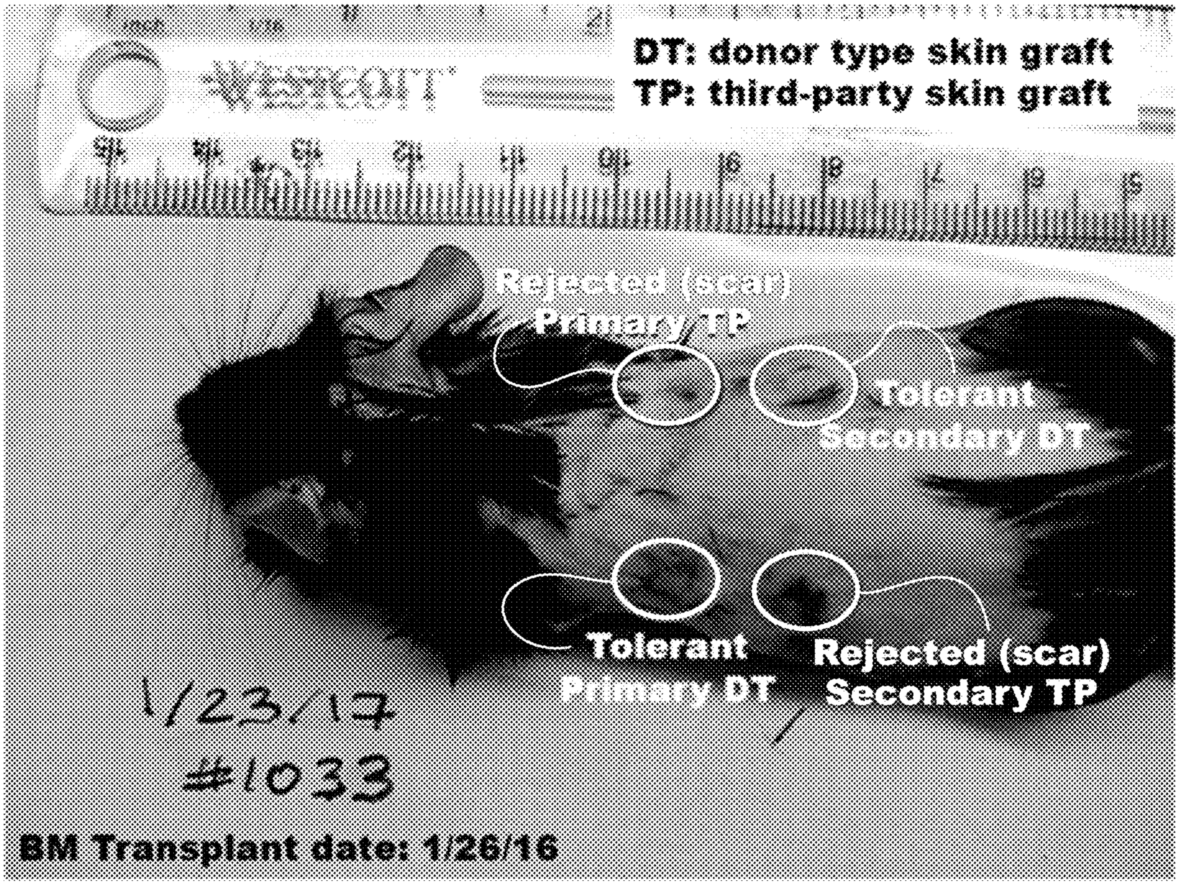
FIG. 3A is a picture of a representative skin graft from the engraftment study reported in FIG. 3B.
Figure 3B:
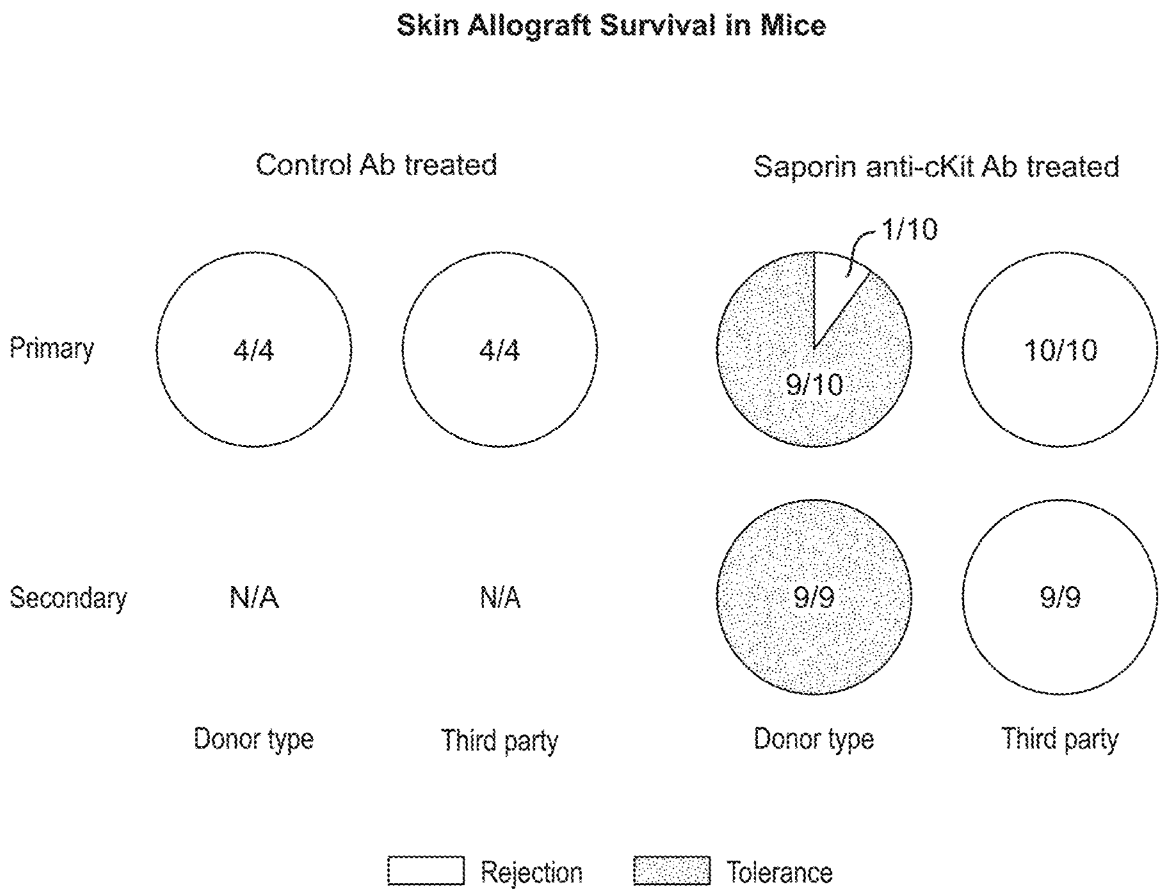
FIG. 3B reports the result of the engraftment study of FIG. 1 and shows that conditioning a recipient with CD117-SAP and infusing with allogeneic bone marrow cells from a donor with transient immunosuppression leads to selective tolerance to proteins/tissues from the same donor.

FIGS. 3A and 3B report durable tolerance of a skin graft from an HLA-mismatched donor in recipients who were treated with an HSC-depleting composition and have also received an infusion of allogeneic bone marrow cells from the HLA-mismatched donor, according to the protocol of FIG. 1. FIG. 3B reports the results of a treatment protocol of FIG. 1, while FIG. 3A is an exemplary picture of skin grafts. As reported in FIG. 3B and shown in FIG. 3A, a recipient conditioned with the HSC-depleting composition and allogeneic bone marrow cells with transient immunosuppression, is tolerant to a skin transplant of the same genetic origin as the allogeneic bone marrow cells. The recipient continues to stay immunocompetent otherwise and has rejected a skin graft from a third-party donor who is HLA-mismatched to the recipient and also to the first donor.

With the present method, patients can tolerate AHSCT from a donor, including an HLA-mismatched donor with a significantly decreased risk of graft-versus-host disease or graft rejection. These patients include HIV-positive patients and patients who are afflicted by a hematological disorder, including, but not limited to, blood cancers and hereditary blood disorders. Blood cancers include leukemias, lymphomas and myelomas. Hereditary blood disorders include hemophilia and hereditary immunodeficiency. Hematological disorders also include acquired immunodeficiency in HIV-positive patients, hemoglobinopathy, fanconi anemia, post-transplant lymphoproliferative disease (PTLD).

Further embodiments provide methods of treatment for an organ or tissue transplant patient. In these methods, HSCs of the patient are first depleted with an HSC-depleting composition. The patient is then administered allogeneic cells selected from bone marrow cells, umbilical cord blood cells, hematopoietic stem and progenitor cells (HSPC), peripheral blood $CD34^+$ cells, peripheral blood $CD34^+$ and $CD90^+$ cells and obtained from a donor. The patient then receives a transplant of an organ, tissue, proteins and/or cells from the same donor. Suitable donors include an HLA-mismatched donor. Suitable donors also include an HLA-matched donor. The patient is also treated with at least one or more of a T-cell/NK-cell depleting or inhibiting antibody or antibody fragment and an immunosuppressive drug. The immunosuppressive treatment can be administered to the patient as many times as needed and for as long as it is needed. Preferably, the immunosuppressive treatment takes place at least before the administration of the allogeneic cells. The immunosuppressive treatment can be also repeated as many times as needed after the administration of the allogeneic cells.

In further embodiments of the method, a transplant recipient can be treated with an HSC-depleting composition and infused with allogeneic cells selected from bone marrow cells, umbilical cord blood cells, hematopoietic stem and progenitor cells (HSPC), peripheral blood $CD34^+$ cells, peripheral blood $CD34^+$ and $CD90^+$ cells, after the recipient has received the transplant, provided that the allogeneic cells originate from the same donor as the transplant. This embodiment can be used for transplant patients in order to decrease or stop administration of an immunosuppressive drug. The method can be also beneficial to a patient in need of treatment for post-transplant lymphoproliferative disease (PTLD). The patient can be further treated with at least one medicament selected from an immunosuppressive drug and T-cell/NK depleting/inhibiting agents.

Various allogeneic transplants are contemplated, including kidney, skin, liver, heart, lung, bone marrow, hair follicles, muscle, ligament, nerve, tendon, bone, limb, face, abdominal wall, eye, ear, or retina. Further examples of allogeneic transplants include hematopoietic stem cells, induced pluripotent stem cells (iPSCs), cells derived from iPSCs, bone marrow cells, islet cells, neurons, hematopoietic cells, epithelial cells, hepatocytes, cardiomyocytes, keratinocytes, embryonic stem cells (ESCs), cells derived from ESCs, mesenchymal stem cells (MSCs), and cells derived from MSCs.

A recipient tolerates well a transplant from an HLA-mismatched donor, if prior to receiving the transplant, the recipient has been conditioned with an HSC-depleting composition followed by an infusion of allogeneic cells selected from bone marrow cells, umbilical cord blood cells, hematopoietic stem and progenitor cells (HSPC), peripheral blood $CD34^+$ cells, and peripheral blood $CD34^+$ and $CD90^+$ cells, and transient immunosuppression by treating a recipient with at least one of T-cell/NK cell depleting or inhibiting agent and/or an immunosuppressive drug.

It has been a common practice prior to the present method to treat a transplant recipient with an immunosuppressive drug after engraftment of the transplant. In the conventional methods, a transplant recipient is required to take an immunosuppressive drug for life. This constitutes a significant burden on a patient's body in part because the patient becomes susceptible to infections, cancers, and other side effects.

One of the technical advantages provided by the present method is the life-long use of an immunosuppressive drug by a transplant recipient can be either decreased, or shortened, or even avoided all together under some circumstances. Another technical advantage provided by the present method is improved access to transplantation as the present method makes tolerable transplants from an HLA-mismatched donor. Another technical advantage provided by the present method is that toxic radiation and chemotherapy is obviated.

Various patients in need of a transplant can benefit from the present method which increases significantly access to transplants. These patients include patients in need of an organ transplant, tissue transplant, protein, and/or cell transplant. These patients include patients suffering from skin burns, cancer patients, patients afflicted by an autoimmune disease, stroke and/or heart attack patients, patients with a spinal cord injury or some other injury, including car accident victims, patients with multiple sclerosis, type I diabetes patients, patients with Alzheimer's disease, patients with Parkinson disease, patients with ulcerative colitis, and patients with congenital or acquired organ failure, such as heart, lung, liver or kidney failure.

Other embodiments include a treatment method in which patient's autologous HSCs are used for infusion instead of or in addition to allogeneic cells selected from bone marrow cells, umbilical cord blood cells, hematopoietic stem and progenitor cells (HSPC), peripheral blood $CD34^+$ cells, and peripheral blood $CD34^+$ and $CD90^+$ cells. This embodiment can be used in treating patients who may benefit from a treatment with a recombinant formulation, but develop an immune reaction to the recombinant formulation as a side effect. Suitable recombinant formulations may include recombinant protein factor VIII for hemophiliac patients as well recombinant insulin for diabetic patients. Other examples of a recombinant protein include Factor IX and iduronidase (IUDA protein). Other recombinant formulations include gene therapy treatments, including those with a recombinant adenovirus, retrovirus or adeno-associated virus (AAV).

In these embodiments, a patient is treated with an HSC-depleting composition and then infused with gene-modified autologous HSCs, wherein the gene-modified autologous HSCs are modified via gene therapy or by gene editing. These embodiments include a method of tolerizing a patient to a recombinant formulation, the method comprising first administering to the patient an HSC-depleting composition, then administering to the patient gene-modified autologous HSCS that give rise to cells tolerant to the recombinant formulation, and then optionally administering to the patient the recombinant formulation, and further optionally immunosuppressing the patient with one or more immunosuppressive drugs and/or T-cell and/or NK-cell depleting or inhibiting antibodies and/or antibody fragments.

In some embodiments, gene-modified autologous HSCs genetically manipulated such that the gene-modified autologous HSCs and their cell progeny become tolerant to a recombinant protein or recombinant virus.

Patients who benefit from this method are patients who may be treated by administering a recombinant protein or other biological preparation, but develop an immune response to the treatment. Such patients may include hemophilia patients treated with functional factor VIII and diabetes patients treated with insulin. Other patients include patients afflicted with an autoimmune disease where the patient's immune system attacks the patient's proteins, including such as diseases as multiple sclerosis and type I diabetes.

Yet another group of patients who can benefit from the present method include patients who may be treated with gene therapy, but are known to develop an immune response to the treatment. Such patients include those treated with a recombinant formulation comprising a recombinant adenovirus, retrovirus, adenovirus-associated virus or some other biological formulation comprising a genetic material to which the patient may develop an immune response.

In this method, a patient is conditioned for a treatment with a recombinant formulation by administering to the patient an HSC-depleting composition, followed by administering to the patient gene-modified autologous HSCs tolerant to the recombinant formulation. In some embodiments of this method, a patient can be treated with one or more medicament selected from T-cell depleting or inhibiting agents, NK-cell depleting or inhibiting agents, and immunosuppressive drugs in order to immunosuppress the patient's immune response. The patient is then treated with the recombinant formulation. At least in some embodiments, the recombinant formulation is administered after the conditioning. In other embodiments, the recombinant combination is administered first, followed by the conditioning. The treatment with a medicament selected from T-cell depleting or inhibiting agents, NK-cell depleting or inhibiting agents, and immunosuppressive drugs can be conducted at any of the stages during conditioning and/or treatment with the recombinant formulation.

Various gene-modified autologous HSCs are contemplated, including those that have been genetically modified to express at least one recombinant protein from the recombinant formulation. For example, autologous HSCs can be gene-modified to express factor VIII in order to condition a patient who will be treated with recombinant factor VIII. For a patient to be treated with recombinant insulin, the patient's autologous HSCs can be gene-modified to express recombinant insulin.

In other embodiments, gene-modified autologous HSCs may express an antigen to which a patient has developed an autoimmune response, including myelin for multiple sclerosis patients and protein-markers expressed on the surface of islet cells for a patient with type I diabetes.

If a recombinant formulation comprises a recombinant virus, such an adenovirus, retrovirus, or adeno-associated virus, the patient's autologous HSCs can be modified to express one or several capsid proteins of the recombinant virus.

Methods for treating patients afflicted with an autoimmune disease are provided as well. An autoimmune disease is to be understood broadly and includes any disorder in which the patient's immune system attaches and damages the patient's own tissues. Autoimmune diseases include diabetes mellitus type 1, Graves disease, inflammatory bowel disease, Crohn's disease, ulcerative colitis, multiple sclerosis, systemic sclerosis, psoriasis, rheumatoid arthritis, immune thrombocytic purpura, systemic lupus erythematosus, juvenile idiopathic arthritis, and autoimmune cytopenia.

In the present method of treatment for an autoimmune disease, the patient's HSCs are depleted with an HSC-depleting composition, the patient is then administered allogeneic cells selected from the group consisting of bone marrow cells, umbilical cord blood cells, hematopoietic stem and progenitor cells (HSPC), peripheral blood $CD34^+$ cells, and peripheral blood $CD34^+$ and $CD90^+$ cells and any combination thereof. The patient can be further treated with a medicament selected from T-cell depleting/inhibiting antibody or antibody fragment, NK-cell depleting/inhibiting antibody or antibody fragment, an immunosuppressive drug, and any combination thereof as many times as needed at any time.

It will be appreciated that administering an HSC-depleting composition according to the present method improves engraftment of HSCs and growth of new blood and immune cells from an HLA-mismatched donor. It will be also appreciated that administering an HSC-depleting composition and engrafting bone marrow or HSCs from an HLA-mismatched donor also improves the likelihood of a successful organ or tissue transplant from the same HLA-mismatched donor. The methods provided in this disclosure improve access to transplants, reduce the risk of complications after transplant, including the risk of graft-versus-host disease and graft failure.

The invention will now be explained by the following non-limiting examples.

Example 1

Depletion of HSCs in male laboratory mice of strain A (C57BL/6 from the Jackson laboratory, Bar Harbor, Maine, USA) was carried out by administering to each of the mice 1.5 mg/kg of an HSC-depleting composition comprising a conjugate in which anti-mouse CD117 antibody (clone 2B8) was linked to saporin by streptavidin-biotin coupling. After 8 days, each recipient mouse has received 20 mln bone marrow cells from male mice of strain B (BALB/c, the Jackson laboratory, Bar Harbor, Maine, USA). Mice of strain B are complete MHC-mismatched donors for mice of strain A.

BALB/c bone marrow cells were obtained by flushing long bones, and were suspended in complete medium containing Ammonium-Chloride-Potassium lysing buffer to remove red blood cells. Unseparated bone marrow cells were injected i.v. into C57BL/6 recipient mice via tail vein. All care and handling of animals was carried out in accordance with guidelines provided in the Guide for the Care and Use of Laboratory Animals published by the U.S. Department of Health and Human Services.

Control mice of strain A have also received the same number of bone marrow cells from mice of strain B, but the control mice were not conditioned with an HSC-depleting composition prior to the bone marrow infusion. Instead, the control group was treated with a control immunoglobulin with no antigenic specificity.

All recipients, including the control group, were then treated under the following immunosuppression protocol. Each recipient mouse received three consecutive 1 mg injections (days 0, 2 and 4 post-bone marrow infusion) of each of the following monoclonal antibodies: rat anti-mouse CD4 (CD4 cell non-depleting; YTS 177), anti-CD40 ligand (MR1) and anti-mouse CD8 (CD8 cell depleting; YTS 169), all from BioXcell (West Lebanon, NH). In addition, two doses of 12 mg/kg of rapamycin (LC Laboratories, Woburn, MA) were administered i.p. at days 6 and 30 post-bone marrow infusion. See FIG. 1 for details of the treatment protocol.

Figure 2C:
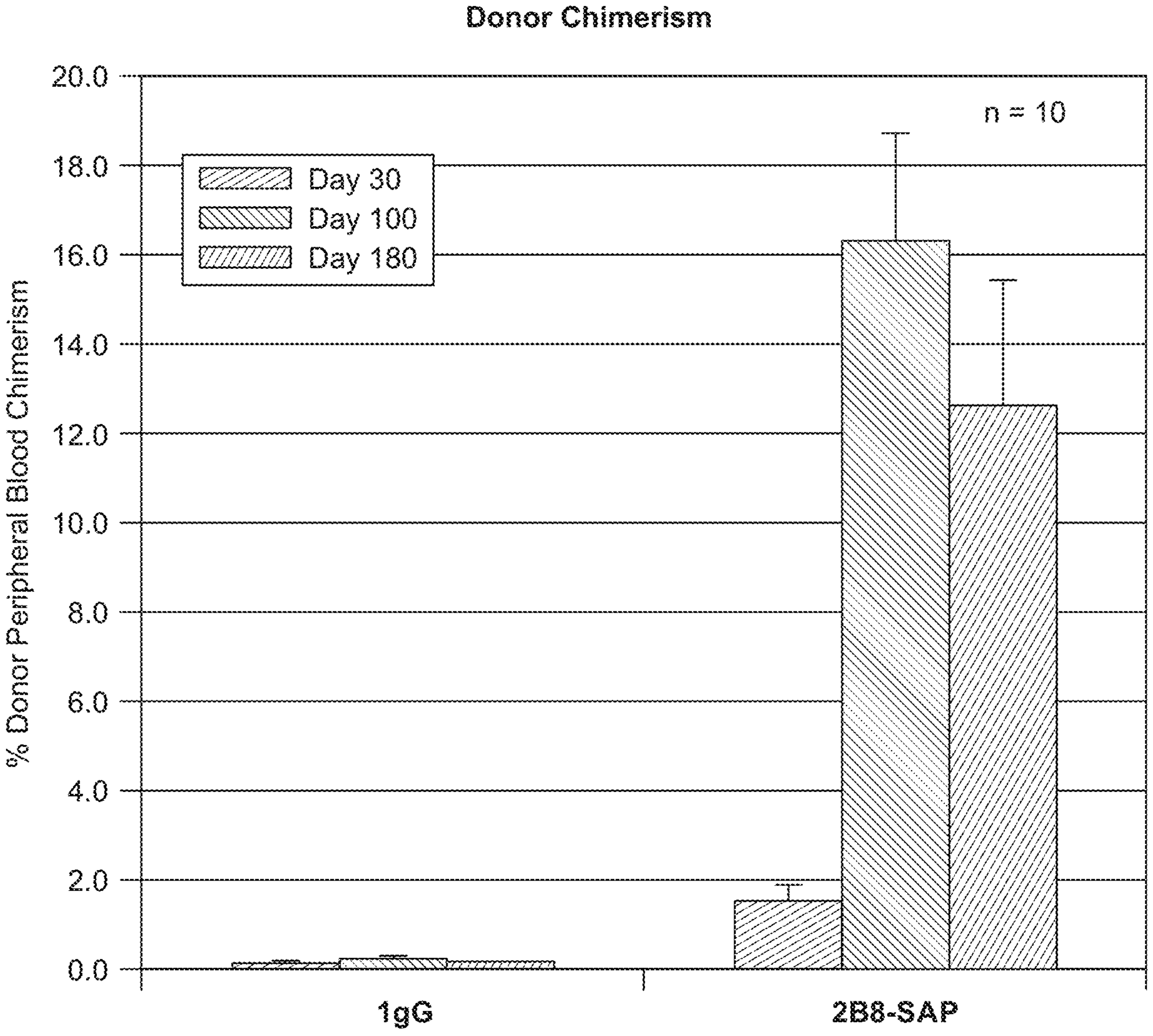
FIG. 2C is a flow cytometry analysis showing that conditioning with CD117-SAP and immune suppression leads to enhanced chimerism in an allogeneic setting.

Chimerism of peripheral blood cells in the recipient mice was analyzed by flow cytometry and the results are reported in FIG. 2A (control group) and FIG. 2B (the present treatment protocol) for each recipient individually, identified by the animal ID number. FIG. 2C is a summary chart for all recipients combined.

The X axis in graphs of FIG. 2A and FIG. 2B stands for the days after bone marrow transplantation. The numbers on Y axis of FIGS. 2A and 2B are the percentage of mononuclear cells that express Balb/c MHC class I (H2Kd) in total mononuclear cells of the peripheral blood in the recipient C57Bl/6 animal. These cells are believed to be donor-derived since H2Kd is only found on Balb/c (strain B) but not on C57Bl/6 cells (Strain A). For this flowcytometry analysis, all viable peripheral blood mononuclear cells were collected and analyzed.

In connection with FIG. 2C, chimerism of peripheral blood cells in the recipient mice was analyzed by flow cytometry 30, 100 or 180 days post bone marrow cell infusion. As shown in FIG. 2C, the recipients treated with an HSC-depleting composition developed a much higher level of chimerism, with about 16% of donor peripheral blood cells being chimeric on day 100, and about 12% on day 180 in comparison to the control group where chimerism was almost undetectable.

Example 2

Depletion of HSCs in male laboratory mice of strain A (C57BL/6 from the Jackson laboratory, Bar Harbor, Maine, USA) was carried out by administering to each of the mice 1.5 mg/kg of an HSC-depleting composition comprising a conjugate in which anti-mouse CD117 antibody (clone 2B8) was linked to saporin by biotin-streptavidin coupling. After 8 days, each recipient mouse has received 20 mln bone marrow cells from male mice of strain B (BALB/c, the Jackson laboratory, Bar Harbor, Maine, USA). Mice of strain B are complete MHC mismatched donors for mice of strain A. All care and handling of animals was carried out in accordance with guidelines provided in the Guide for the Care and Use of Laboratory Animals published by the U.S. Department of Health and Human Services.

All recipients were treated under the following immunosuppression protocol. Each recipient mouse received three consecutive 1 mg injections (days 0, 2 and 4 post-bone marrow infusion) of each of the following monoclonal antibodies: rat anti-mouse CD4 (CD4 cell non-depleting; YTS 177), anti-CD40 ligand (MR1) and anti-mouse CD8 (CD8 cell depleting; YTS 169), all from BioXcell (West Lebanon, NH). In addition, two doses of 12 mg/kg of rapamycin (LC Laboratories, Woburn, MA) were administered i.p. at days 6 and 30 post-bone marrow infusion. See FIG. 1 for details of the treatment protocol.

The primary skin transplantation was then performed on day 90 post-bone marrow infusion. The secondary skin transplantation was performed on day 180 post-bone marrow infusion. Each skin graft was full thickness tail skin measuring 1×1 cm on a lateral flank of a recipient mouse of strain A. During the primary skin transplantation, each recipient mouse received one skin graft from the BALB/c donor type (Strain B) and one from unrelated Strain C (CBA/Ca mice from the Jackson laboratory, Bar Harbor, Maine, USA). During the secondary skin transplantation, the same grafting protocol was repeated. See FIG. 1 for the engraftment protocol.

All primary skin grafts were transplanted on day 90 after the bone marrow infusion from the donor (Strain B). All secondary skin grafts were transplanted on day 180 after bone marrow infusion from the donor (Strain B). As shown in FIG. 1, no additional immunosuppression treatments were carried out between the primary and secondary skin grafts, and no additional immunosuppression treatments were carried out after transplantation of the secondary skin graft. All skin grafts were observed daily after the removal of the bandage at day 7 post-transplantation. Skin grafts were considered rejected when a complete loss of viable donor epithelium had occurred.

As reported in FIG. 3A and FIG. 3B, conditioned recipients tolerated well a primary donor type (DT) skin graft and a secondary donor type (DT) skin graft, both skin grafts originating from strain B. At the same time, both skin grafts (primary and secondary) from a third-party strain C were rejected. See the "saporin anti-cKit Ab treated" group on the right of FIG. 3B. See also a picture of the exemplary graft from this group in FIG. 3A.

At the same time, recipients in the control group not conditioned with an HSC-depleting composition, but otherwise treated with bone marrow cells and immunosuppressed in the same way as the treatment protocol group, have rejected the skin grafts from the donor. See the "control Ab treated" group on the left of FIG. 3B.

This supports a conclusion that conditioning a recipient with an HSC-depleting composition and infusing the recipient with allogeneic bone marrow cells from an HSC-mismatched donor makes the recipient tolerant specifically to an allogeneic tissue graft from the HSC-mismatched donor, while the recipient advantageously also continues to be immunocompetent and capable of rejecting other allogeneic grafts from other unrelated donors.

What is claimed is:

1. A method of tolerizing a patient to a recombinant formulation, the method comprising:

administering to the patient a CD117 antibody or antibody fragment with specific binding affinity to a protein displayed at the HSC surface, said antibody or antibody fragment being coupled with a toxin;

administering to the patient gene-modified autologous HSCs that give rise to cells which are tolerant to a recombinant formulation;

administering to the patient the recombinant formulation; and administering to the patient a medicament selected from the group consisting of a T-cell depleting or inhibiting antibody or antibody fragment, natural killer (NK) cell depleting or inhibiting antibody or fragment, immunosuppressive drug, and any combination thereof, wherein the medicament is administered during a time period selected from the group consisting of: prior to the administration of the HSC-depleting composition; during administration of the HSC-depleting composition; after the administration of the HSC-depleting composition, but before the administration of the gene-modified autologous HSCs; during administration of the gene-modified autologous HSCs; after the administration of the gene-modified autologous HSCs; after the administration of the recombinant formulation; and any combination thereof.

2. The method of claim 1, wherein the recombinant formulation is selected from the group consisting of a recombinant adeno-associated virus (AAV), adenovirus, factor VIII, and factor IX.

* * * * *